United States Patent [19]
Ng et al.

[11] Patent Number: 5,583,238
[45] Date of Patent: Dec. 10, 1996

[54] METHOD FOR MAKING INTERMEDIATES USEFUL IN SYNTHESIS OF RETROVIRAL PROTEASE INHIBITORS

[75] Inventors: John S. Ng, Chicago; Claire A. Przybyla, Sed Plaines; Richard A. Mueller, Glencoe; Michael L. Vazquez, Gurnee, all of Ill.; Daniel P. Getman, Chesterfield, Mo.

[73] Assignee: G. D. Searle & Co., Chicago, Ill.

[21] Appl. No.: 290,976

[22] PCT Filed: May 24, 1993

[86] PCT No.: PCT/US93/04804

§ 371 Date: Dec. 16, 1994

§ 102(e) Date: Dec. 16, 1994

[87] PCT Pub. No.: WO93/23388

PCT Pub. Date: Nov. 25, 1993

Related U.S. Application Data

[63] Continuation-in-part of Ser. No. 886,558, May 20, 1992, Pat. No. 5,482,947, which is a continuation-in-part of Ser. No. 789,646, Nov. 14, 1991, abandoned, which is a continuation-in-part of Ser. No. 615,210, Nov. 19, 1990, abandoned.

[51] Int. Cl.⁶ .................... C07D 301/00; C07D 209/48
[52] U.S. Cl. .................... 549/519; 548/465; 548/517
[58] Field of Search .................... 549/519; 548/469, 548/517

[56] References Cited

U.S. PATENT DOCUMENTS

| | | | |
|---|---|---|---|
| H725 | 1/1990 | Gordon | 514/307 |
| 4,268,688 | 5/1981 | Tinker et al. | 546/325 |
| 4,477,441 | 10/1984 | Boger et al. | 514/295 |
| 4,514,391 | 4/1985 | Gordon et al. | 514/306 |
| 4,548,926 | 10/1985 | Matsueda et al. | 514/317 |
| 4,599,198 | 7/1986 | Hoover | 514/317 |
| 4,616,088 | 10/1986 | Ryono et al. | 514/296 |
| 4,668,769 | 5/1987 | Hoover | 514/301 |
| 4,668,770 | 5/1987 | Boger et al. | 514/252 |
| 4,757,050 | 7/1988 | Natarajan et al. | 546/195 |
| 4,963,530 | 10/1990 | Hemmi et al. | 514/196 |
| 4,977,277 | 12/1990 | Rosenberg et al. | 548/217 |
| 4,990,669 | 2/1991 | Reetz et al. | 546/318 |
| 5,157,041 | 10/1992 | Handa et al. | 514/295 |

FOREIGN PATENT DOCUMENTS

| | | |
|---|---|---|
| 0342541 | of 0000 | European Pat. Off. . |
| 0104041 | of 0000 | European Pat. Off. . |
| 0114993 | 8/1984 | European Pat. Off. . |
| 0172347 | 2/1986 | European Pat. Off. . |
| 0223437 | 5/1987 | European Pat. Off. . |
| 0264795 | 4/1988 | European Pat. Off. . |
| 0337714 | 10/1989 | European Pat. Off. . |
| 0346847 | 12/1989 | European Pat. Off. . |
| 0356223 | 2/1990 | European Pat. Off. . |
| 0393457 | 10/1990 | European Pat. Off. . |
| 0393445 | 10/1990 | European Pat. Off. . |
| 0389898 | 10/1990 | European Pat. Off. . |
| 0402646 | 12/1990 | European Pat. Off. . |
| 2184730 | 7/1987 | United Kingdom . |
| 2209752 | 5/1989 | United Kingdom . |
| WO84/03044 | 8/1984 | WIPO . |
| WO92/14703 | 9/1992 | WIPO . |
| WO93/13066 | 7/1993 | WIPO . |

OTHER PUBLICATIONS

Hoffmann et. al., *J. Chem. Soc., Chem. Commun.*, p. 195–196, Mar. 1991.
Roberts et al, *Science*, 248, 358 (1990).
Krohn et al, *J. Med. Chem.*, 34, 3340 (1991).
Getman et al, *J. Med. Chem.*, 36, 288 (1993).
Reetz et al, *Tet. Lett.*, 30, 5425 (1989).
Sax, N. I., "Dangerous Properties of Industrial Materials", 6th Ed., Van Nostrand Reinhold Co., 1984, p. 433.
"Handbook of Reactive Chemical Hazards", 3rd Ed., Butterworths, 1985, p. 295.
Matteson et al, *Synlett.*, 631 (1991).
Reetz et al, *Angew. Chem. Int. Ed.*, 26, 1141–1143 (1987).
J. R. Parikh, *J. Amer. Chem. Soc.*, 89, 5505–5507 (1967).
Erickson et al, *Science*, 249: 527–533 (1990).
Drugs of the Future, 1991, 16(3), 210–212.
Meek et al, *Nature*, 343:90–92, (1990).
Pept. Struct. Funct. Proc. Am. Pept. Sym. 8th ed. by V. J. Hunby and D. H. Rich, pp. 511–520 (1983).
McQuade et al, "A Synthetic HIV–1 Protease Inhibitor with Antiviral Activity Arrests HIV–Like Particle Maturation", *Science*, 274, 454 (1990).
Rosenberg et al, *J. Med. Chem.*, 30, 1224–1228 (1987).
Sadhu et al, *Tet. Lett.* 27, 795 (1986).
Villieras et al, *Tet. Lett.*, 25, 835 (1984).
Fittkau, *J. Prakt. Chem*, 315, 1037–1044 (1973).
Evans et al, *J. Org. Chem.*, vol. 50, No. 23, 4615–24 (1985).
Michnick et al, *Synlett*, 9:631–2 (1991).

*Primary Examiner*—Bernard Dentz
*Attorney, Agent, or Firm*—Frank S. Ungemach, Esq.

[57] ABSTRACT

A synthesis is described for intermediates which are readily amenable to the large scale preparation of hydroxyethylurea-based chiral HIV protease inhibitors. The method includes forming a diastereoselective epoxide from a chiral alpha amino aldehyde.

14 Claims, No Drawings

METHOD FOR MAKING INTERMEDIATES USEFUL IN SYNTHESIS OF RETROVIRAL PROTEASE INHIBITORS

This application is 371 of PCT/US93/04804 filed May 24, 1993, which is a continuation in part of patent application Ser. No. 07/886,558, filed May 20, 1992, now U.S. Pat. No. 5,482,947, which is a continuation in part of PCT/US91/8613, filed Nov. 18, 1991, which is a continuation in part of U.S. Pat. No. 07/789,646, filed Nov. 14, 1991, now abandoned, which is a continuation in part of U.S. patent application Ser. No. 7/615,210, filed Nov. 19, 1990, now abandoned.

BACKGROUND OF THE INVENTION

1. Field of the Invention

Synthesis of many HIV protease inhibitors containing a hydroxyethylamine or hydroxyethylurea isostere include the amine opening of a key intermediate chiral epoxide. The synthesis of the key chiral epoxide requires a multi-step synthesis starting from L-phenylalanine and results in a low overall yield. The diastereoselectivity of the reduction step of the intermediate amino chloromethylketone is low and use of explosive diazomethane prevents the scale up of the method to multikilogram productions. The present invention relates to a method of preparing retroviral protease inhibitors and more particularly to a diastereoselective method of forming chiral intermediates for the preparation of urea containing hydroxyethylamine protease inhibitors.

2. Related Art

Roberts et al, *Science*, 248, 358 (1990), Krohn et al, *J. Med, Chem*. 344, 3340 (1991) and German, et al, *J. Med. Chem.*, 346, 288 (1993) have previously reported synthesis of protease inhibitors containing the hydroxyethylamine or hydroxyethylurea isostere which include the opening of an epoxide generated in a multi-step synthesis starting from an amino acid. These methods also contain steps which include diazomethane and the reduction of an amino chloromethyl ketone intermediate to an amino alcohol prior to formation of the epoxide. The overall yield of these syntheses are low and the use of explosive diazomethane additionally prevents such methods from being commercially acceptable.

Tinker et al U.S. Pat. No. 4,268,688 discloses a catalytic process for the asymmetric hydroformylation to prepare optically active aldehydes from unsaturated olefins. Similarly, Reetz et al U.S. Pat. No. 4,990,669 discloses the formation of optically active alpha amino aldehydes through the reduction of alpha amino carboxylic acids or their esters with lithium aluminum hydride followed by oxidation of the resulting protected beta amino alcohol by dimethyl sulfoxide/oxalyl chloride or chromium trioxide/pyridine. Alternatively, protected alpha amino carboxylic acids or esters thereof can be reduced with diisobutylaluminum hydride to form the protected amino aldehydes.

Reetz et al (Tet. Lett., 30, 5425 (1989)) disclosed the use of sulfonium and arsonium ylides and their reactions of protected α-amino aldehydes to form aminoalkyl epoxides. This method suffers from the use of highly toxic arsonium compounds or the use of combination of sodium hydride and dimethyl sulfoxide which is extremely hazardous in large scale. (Sodium hydride and DMSO are incompatible: Sax, N. I., "Dangerous Properties of Industrial Materials", 6th Ed., Van Nostraud Reinhold Co., 1984, p. 433. Violent explosions have been reported on the reaction of sodium hydride and excess DMSO, "Handbook of Reactive Chemical Hazards", 3rd Ed., Butterworths, 1985, p. 295. Matteson et al *Synlett.*, 1991, 631 reported the addition of chloromethyllithium or bromomethyllithium to racemic aldehydes.

Tet. Letters, Vol. 27, No. 7, 1986, pages 795–798 discloses in general the oxidation of carbonyl compounds to epoxides or chlorohydrines using chloro- or bromomethyllithium. The reference however is silent about amino aldehydes as well as optically active compounds.

SUMMARY OF THE INVENTION

Human immunodeficiency virus (HIV), the causative agent of acquired immunodeficiency syndrome (AIDS), encodes three enzymes, including the well-characterized proteinase belonging to the aspartic proteinase family, the HIV protease. Inhibition of this enzyme is regarded as a promising approach for treating AIDS. One potential strategy for inhibitor design involves the introduction of hydroxyethylene transition-state analogs into inhibitors. Inhibitors adapting the hydroxyethylamine or hydroxyethylurea isostere are found to be highly potent inhibitors of HIV proteases. Despite the potential clinical importance of these compounds, previously there were no satisfactory synthesis which could be readily and safely scaled up to prepare large kilogram quantities of such inhibitors needed for development and clinical studies. This invention provides an efficient synthesis of intermediates which are readily amenable to the large scale preparation of hydroxyethylurea-based chiral HIV protease inhibitors.

Specifically, the method includes preparing a diastereoselective epoxide from a chiral alpha amino aldehyde.

DETAILED DESCRIPTION OF THE INVENTION

This invention relates to a method of preparation of HIV protease inhibitor that allows the preparation of commercial quantities of intermediates of the formula

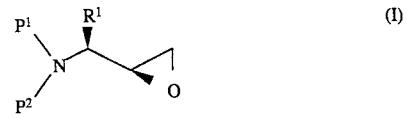

wherein $R^1$ is selected from alkyl, aryl, cycloalkyl, cycloalkylalkyl and arylalkyl, which are optionally substituted with a group selected from alkyl, halogen, $NO^2$, $OR^9$ or $SR^9$, where $R^9$ represents hydrogen or alkyl; and $p^1$ and $p^2$ independently are selected from amine protecting groups, including but not limited to, arylalkyl, substituted arylalkyl, cycloalkenylalkyl and substituted cycloalkenylalkyl, allyl, substituted allyl, acyl, alkoxycarbonyl, aralkoxycarbonyl and silyl. Examples of arylalkyl include, but are not limited to benzyl, ortho-methylbenzyl, trityl and benzhydryl, which can be optionally substituted with halogen, alkyl of $C_1$–$C_8$, alkoxy, hydroxy, nitro, alkylene, amino, alkylamino, acylamino and acyl, or their salts, such as phosphonium and ammonium salts. Examples of aryl groups include phenyl, naphthalenyl, indanyl, anthracenyl, durenyl, 9-(9-phenylfluorenyl) and phenanthrenyl, cycloalkenylalkyl or substituted cycloalkenylalkyl radicals containing cycloalkyls of $C_6$–$C_{10}$. Suitable acyl groups include carbobenzoxy, t-butoxycarbonyl, isobutoxycarbonyl, benzoyl, substituted benzoyl, butyryl, acetyl, tri-fluoroacetyl, tri-chloroacetyl, phthaloyl and the like.

Additionally, the $p^1$ and/or $p^2$ protecting groups can form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, e.g., nitrophthalimidyl. The term silyl refers to a silicon atom optionally substituted by one or more alkyl, aryl and aralkyl groups.

Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of the amine functions to provide mono- or bis-disilylamine can provide derivatives of the aminoalcohol, amino acid, amino acid esters and amino acid amide. In the case of amino acids, amino acid esters and amino acid amides, reduction of the carbonyl function provides the required mono- or bis-silyl aminoalcohol. Silylation of the aminoalcohol can lead to the N,N,O-tri-silyl derivative. Removal of the silyl function from the silyl ether function is readily accomplished by treatment with, for example, a metal hydroxide or ammonium fluoride reagent, either as a discrete reaction step or in situ during the preparation of the amino aldehyde reagent. Suitable silylating agents are, for example, trimethylsilyl chloride, tert-buty-dimethylsilyl chloride, phenyldimethylsilyl chloride, diphenylmethylsilyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Preferably $p^1$, $p^2$ and $R^1$ are independently selected from aralkyl and substituted aralkyl. More preferably, each of $p^1$, $p^2$ and $R^1$ is benzyl.

Protected alpha-aminoaldehyde intermediates of the formula:

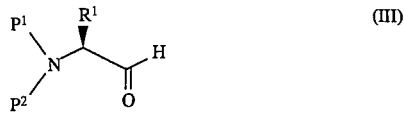

(III)

and protected chiral alpha-amino alcohols of the formula:

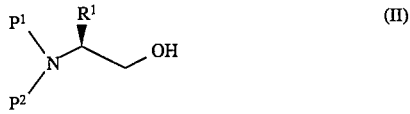

(II)

wherein $p^1$, $p^2$ and $R^1$ are as defined above, are also described herein.

As utilized herein, the term "amino epoxide" alone or in combination, means an amino-substituted alkyl epoxide wherein the amino group can be a primary, or secondary amino group containing substituents selected from hydrogen, and alkyl, aryl, aralkyl, alkenyl, alkoxycarbonyl, aralkoxycarbonyl, cycloalkenyl, silyl, cycloalkylalkenyl radicals and the like and the epoxide can be alpha to the amine. The term "amino aldehyde" alone or in combination, means an amino-substituted alkyl aldehyde wherein the amino group can be a primary, or secondary amino group containing substituents selected from hydrogen, and alkyl, aryl, aralkyl, alkenyl, aralkoxycarbonyl, alkoxycarbonyl, cycloalkenyl, silyl, cycloalkylalkenyl radicals and the like and the aldehyde can be alpha to the amine. The term "alkyl", alone or in combination, means a straight-chain or branched-chain alkyl radical containing from 1 to about 10, preferably from 1 to about 8, carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radial having one or more double bonds and containing from 2 to about 18 carbon atoms preferably from 2 to about 8 carbon atoms. Examples of suitable alkenyl radicals include ethenyl, propenyl, allyl, 1,4-butadienyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkenyl", alone or in combination, means an alkyl radical which contains from about 3 to about 8 carbon atoms and is cyclic and which contains at least one double bond in the ring which is non-aromatic in character. The term "cycloalkenylalkyl" means cycloalkenyl radical as defined above which is attached to an alkyl radical, the cyclic portion containing from 3 to about 8, preferably from 3 to about 6, carbon atoms. Examples of such cycloalkyl radicals include cyclopropyl, cyclobutyl, cyclopentyl, cyclohexyl and the like. Examples of such cycloalkenyl radicals include cyclopropenyl, cyclobutenyl, cyclopentenyl, cyclohexenyl, dihydrophenyl and the like. The term "aryl", alone or in combination, means a carbocyclic aromatic system containing one, two or three rings wherein such rings may be attached together in a pendent manner or may be fused. Examples of "aryl" include phenyl or naphthyl radical either of which optionally carries one or more substituents selected from alkyl, alkoxy, halogen, hydroxy, amino, nitro and the like, as well as p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. Examples of substituted aralkyl include 3,5-dimethoxybenzyl bromide, 3,4-dimethoxybenzyl bromide, 2,4-dimethoxybenzyl bromide, 3,4,5-trimethoxybenzyl bromide, 4-nitrobenzyl iodide, 2,6-dichlorobenzyl bromide, 1,4-bis(chloromethyl)benzene, 1,2-bis(bromomethyl)benzene, 1,3-bis(chloromethyl)benzene, 4-chlorobenzyl chloride, 3-chlorobenzyl chloride, 1,2-bis(chloromethyl)benzene, 6-chloropiperonyl chloride, 2-chlorobenzyl chloride, 4-chloro-2-nitrobenzyl chloride, 2-chloro-6-fluorobenzyl chloride, 1,2-bis(chloromethyl)-4,5-dimethylbenzene, 3,6-bis(chloromethyl)durene, 9,10-bis(chloromethyl)anthracene, 2,5-bis(chloromethyl)-p-xylene, 2,5-bis(chloromethyl)-1,4-dimethoxybenzene, 2,4-bis(chloromethyl)anisole, 4,6-(dichloromethyl)-m-xylene, 2,4-bis(chloromethyl)mesitylene, 4-(bromomethyl)3,5-dichlorobenzophenone, n-(alpha-chloro-o-tolyl)benzylamine hydrochloride, 3-(chloromethyl)benzoyl chloride, 2-chloro-4-chloromethyltoluene, 3,4-dichlorobenzyl bromide, 6-chloro-8-chloromethylbenzo-1,3-dioxan, 4- (2,6-dichlorobenzylsulphonyl)benzylbromide, 5-(4-chloromethylphenyl)-3-(4-chlorophenyl)-1,2,4-oxadiazole, 5-(3-chloromethylphenyl)-3-(4-chlorophenyl)-1,2,4-oxadiazole, 4-(chloromethyl)benzoyl chloride, di(chloromethyl)toluene, 4-chloro-3-nitrobenzyl chloride, 1-(dimethylchlorosilyl)-2-(p, m-chloromethylphenyl)ethane, 1-(dimethylchlorosilyl)-2- (p, m-chloromethylphenyl)ethane, 3-chloro-4-methoxybenzyl chloride, 2,6-bis(chloromethyl)-4-methylphenol, 2,6-bis(chloromethyl)-p-tolyl acetate, 4-bromobenzyl bromide, p-bromobenzoyl bromide, alpha alpha'-dibromo-m-xylene, 3-bromobenzyl bromide, 2-bromobenzyl bromide, 1,8-bis(bromomethyl)naphthalene, o-xylylene dibromide, p-xylylene dibromide, 2,2'-bis(bromomethyl)-1,1'-biphenyl, alpha, alpha'-dibromo-2,5-dimethoxy-p-xylene, benzyl chloride, benzyl bromide, 4,5-bis(bromomethyl)phenanthrene, 3-(bromomethyl)benzyltriphenylphosphonium bromide, 4-(bromomethyl)benzyltriphenylphosphonium bromide, 2-(bromomethyl)benzyltriphenylphosphonium bromide, 1-(2-bromoethyl )-2-(bromomethyl)-4-nitrobenzene, 2-bromo-5-fluorobenzylbromide, 2,6-bis(bromomethyl) fluorobenzene, o-bromomethylbenzoyl bromide, p-bromomethyl benzoyl bromide, 1-bromo-2-(bromomethyl)naphthalene, 2-bromo-5-methoxybenzyl bromide, 2,4-dichlorobenzyl chloride, 3,4-dichlorobenzyl chloride, 2,6-dichlorobenzyl chloride, 2,3-dichlorobenzyl chloride, 2,5-dichlorobenzyl chloride, methyldichlorosilyl(chloromethylphenyl)ethane, methyldichlorosilyl(chloromethylphenyl)ethane, methyldichlorosilyl(chloromethylphenyl)ethane, 3,5-dichlorobenzyl chloride, 3,5-dibromo-2-hydroxybenzyl bromide, 3,5-dibromobenzyl bromide, p-(chloromethyl)phenyltrichlorosilane, 1-trichlorosilyl-2-(p,m-chloromethylphenyl)ethane, 1-trichlorosilyl-2-(p,m-chloromethylphenyl)ethane, 1,2,4,5-tetrakis(bromomethyl)benzene. The term aralkoxycarbonyl means an aralkoxyl group attached to a carbonyl. Carbobenzoxy is an example of aralkoxycarbonyl. The term "heterocyclic ring system" means a saturated or partially unsaturated monocyclic, bicyclic or tricyclic heterocycle which contains one or more hetero atoms as ring atoms, selected from nitrogen, oxygen, silicon and sulphur, which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e. =N—) by oxido and which is attached via a carbon atom. Examples of such heterocyclic groups are pyrrolidinyl, piperidinyl, piperazinyl, morpholinyl, thiamorpholinyl, pyrrolyl, phthalimide, succinimide, maleimide, and the like. Also included are heterocycles containing two silicon atoms simultaneously attached to the nitrogen and joined by carbon atoms. The term "alkylamino" alone or in combination, means an amino-substituted alkyl group wherein the amino group can be a primary, or secondary amino group containing substituents selected from hydrogen, and alkyl, aryl, aralkyl, cycloalkyl, cycloalkylalkyl radicals and the like. The term "halogen" means fluorine, chlorine, bromine or iodine. The term dihaloalkyl means two halogen atoms, the same or different, substituted on the same carbon atom. The term "oxidizing agent" includes a single agent or a mixture of oxidizing reagents. Examples of mixtures of oxidizing reagents include sulfur trioxidepyridine/dimethylsulfoxide, oxalyl chloride/dimethyl sulfoxide, acetyl chloride/dimethyl sulfoxide, acetyl anhydride/dimethyl sulfoxide, trifluoroacetyl chloride/dimethyl sulfoxide, toluenesulfonyl bromide/dimethyl sulfoxide, phosphorous pentachloride/dimethyl sulfoxide and isobutylchloroformate/dimethyl sulfoxide.

A general Scheme for the preparation of amino epoxides, useful as intermediates in the synthesis of HIV protease inhibitors is shown in Scheme 1 below.

Scheme I

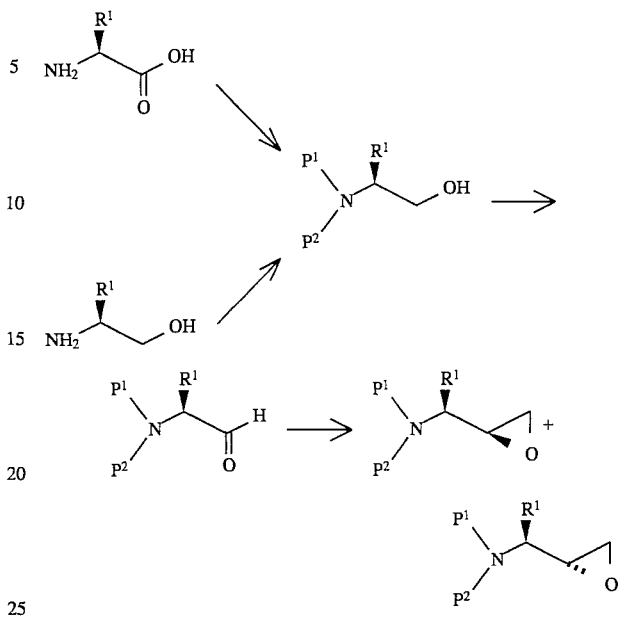

The economical and safe large scale method of preparation of protease inhibitors of the present invention can alternatively utilize amino acids or amino alcohols to form N,N-protected alpha aminoalcohol of the formula

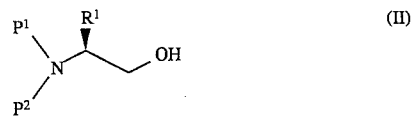

(II)

wherein $p^1$, $p^2$ and $R^1$ are described above.

Whether the compounds of Formula II are formed from amino acids or aminoalcohols, such compounds have the amine protected with groups $p^1$ and $p^2$ as previously identified. The nitrogen atom can be alkylated such as by the addition of suitable alkylating agents in an appropriate solvent in the presence of base.

Alternate bases used in alkylation include sodium hydroxide, sodium bicarbonate, potassium hydroxide, lithium hydroxide, potassium carbonate, sodium carbonate, cesium hydroxide, magnesium hydroxide, calcium hydroxide or calcium oxide, or tertiary amine bases such as triethyl amine, diisopropylethylamine, N-methylpiperidine, pyridine, dimethylaminopyridine and azabicyclononane. Reactions can be homogenous or heterogenous. Suitable solvents are water and protic solvents or solvents miscible with water, such as methanol, ethanol, isopropyl alcohol, tetrahydrofuran and the like, with or without added water. Dipolar aprotic solvents may also be used with or without added protic solvents including water. Examples of dipolar aprotic solvents include acetonitrile, dimethylformamide, dimethyl acetamide, acetamide, tetramethyl urea and its cyclic analog, dimethylsulfoxide, N-methylpyrrolidone, sulfolane, nitromethane and the like. Reaction temperature can range between about −20° to 100° C. with the preferred temperature of about 25°–85° C. The reaction may be carried out under an inert atmosphere such as nitrogen or argon, or normal or dry air, under atmospheric pressure or in a sealed reaction vessel under positive pressure. The most preferred alkylating agents are benzyl bromide or benzyl chloride or monosubstituted aralkyl halides or polysubstituted aralkyl halides. Sulfate or sulfonate esters are also suitable reagents to provide the corresponding benzyl analogs and they can be preformed from the corresponding benzyl alcohol or formed in situ by methods well known to those skilled in the art. Trityl, benzhydryl, substituted trityl and substituted benzhydryl groups, independently, are also effective amine protecting groups [p$^1$, p$^2$] as are allyl and substituted allyl groups. Their halide derivatives can also be prepared from the corresponding alcohols by methods well known to those skilled in the art such as treatment with thionyl chloride or bromide or with phosphorus tri- or pentachloride, bromide or iodide or the corresponding phosphoryl trihalide. Examples of groups that can be substituted on the aryl ring include alkyl, alkoxy, hydroxy, nitro, halo and alkylene, amino, mono- and dialkyl amino and acyl amino, acyl and water solubilizing groups such as phosphonium salts and ammonium salts. The aryl ring can be derived from, for example, benzene, napthelene, indane, anthracene, 9-(9-phenyl fluorenyl, durene, phenanthrene and the like. In addition, 1,2-bis (substituted alkylene) aryl halides or sulfonate esters can be used to form a nitrogen containing aryl or non-aromatic heterocyclic derivative [with p$^1$ and p$^2$] or bis-heterocycles. Cycloalkylenealkyl or substituted cyloalkylene radicals containing 6–10 carbon atoms and alkylene radicals constitute additional acceptable class of substituents on nitrogen prepared as outlined above including, for example, cyclohexylenemethylene.

Compounds of Formula II can also be prepared by reductive alkylation by, for example, compounds and intermediates formed from the addition of an aldehyde with the amine and a reducing agent, reduction of a Schiff Base, carbinolamine or enamine or reduction of an acylated amine derivative. Reducing agents include metals [platinum, palladium, palladium hydroxide, palladium on carbon, platinum oxide, rhodium and the like] with hydrogen gas or hydrogen transfer molecules such as cyclohexene or cyclohexadiene or hydride agents such as lithium aluminumhydride, sodium borohydride, lithium borohydride, sodium cyanoborohydride, diisobutylaluminum hydride or lithium tri-tert-butoxyaluminum hydride.

Additives such as sodium or potassium bromide, sodium or potassium iodide can catalyze or accelerate the rate of amine alkylation, especially when benzyl chloride was used as the nitrogen alkylating agent.

Phase transfer catalysis wherein the amine to be protected and the nitrogen alkylating agent are reacted with base in a solvent mixture in the presence of a phase transfer reagent, catalyst or promoter. The mixture can consist of, for example, toluene, benzene, ethylene dichloride, cyclohexane, methylene chloride or the like with water or a aqueous solution of an organic water miscible solvent such as THF. Examples of phase transfer catalysts or reagents include tetrabutylammonium chloride or iodide or bromide, tetrabutylammonium hydroxide, tri-butyloctylammonium chloride, dodecyltrihexylammonium hydroxide, methyltrihexylammonium chloride and the like.

A preferred method of forming substituted amines involves the aqueous addition of about 3 moles of organic halide to the amino acid or about 2 moles to the aminoalcohol. In a more preferred method of forming a protected amino alcohol, about 2 moles of benzylhalide in a basic aqueous solution is utilized. In an even more preferred method, the alkylation occurs at 50° C. to 80° C. with potassium carbonate in water, ethanol/water or denatured ethanol/water. In a more preferred method of forming a protected amino acid ester, about 3 moles of benzylhalide is added to a solution containing the amino acid.

The protected amino acid ester is additionally reduced to the protected amino alcohol in an organic solvent. Preferred reducing agents include lithium aluminiumhydride, lithium borohydride, sodium borohydride, borane, lithium tri-terbutoxyaluminum hydride, borane. THF complex. Most preferably, the reducing agent is diisobutylaluminum hydride (DiBAL-H) in toluene. These reduction conditions provide an alternative to a lithium aluminum hydride reduction.

Purification by chromatography is possible. In the preferred purification method the alpha amino alcohol can be purified by an acid quench of the reaction, such as with hydrochloric acid, and the resulting salt can be filtered off as a solid and the amino alcohol can be liberated such as by acid/base extraction.

The protected alpha amino alcohol is oxidized to form a chiral amino aldehyde of the formula

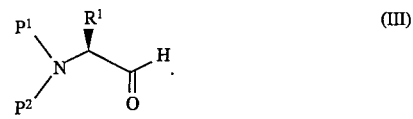

Acceptable oxidizing reagents include, for example, sulfur trioxide-pyridine complex and DMSO, oxalyl chloride and DMSO, acetyl chloride or anhydride and DMSO, trifluoroacetyl chloride or anhydride and DMSO, methanesulfonyl chloride and DMSO or tetrahydrothiaphene-S-oxide, toluenesulfonyl bromide and DMSO, trifluoromethanesulfonyl anhydride (triflic anhydride) and DMSO, phosphorus pentachloride and DMSO, dimethylphosphoryl chloride and DMSO and isobutylchloroformate and DMSO. The oxidation conditions reported by Reetz et al [*Angew Chem.*, 99, p. 1186, (1987)], *Angew Chem. Int. Ed. Engl.*, 26, p. 1141, 1987) employed oxalyl chloride and DMSO at –78° C.

The preferred oxidation method described in this invention is sulfur trioxide pyridine complex, triethylamine and DMSO at room temperature. This system provides excellent yields of the desired chiral protected amino aldehyde usable without the need for purification i.e., the need to purify kilograms of intermediates by chromatography is eliminated and large scale operations are made less hazardous. Reaction at room temperature also eliminated the need for the use of low temperature reactor which makes the process more suitable for commercial production.

The reaction may be carried out under an inert atmosphere such as nitrogen or argon, or normal or dry air, under atmospheric pressure or in a sealed reaction vessel under positive pressure. Preferred is a nitrogen atmosphere. Alternative amine bases include, for example, tri-butyl amine, tri-isopropyl amine, N-methylpiperidine, N-methyl morpholine, azabicyclononane, diisopropylethylamine, 2,2,6,6-tetramethylpiperidine, N,N-dimethylaminopyridine, or mixtures of these bases. Triethylamine is a preferred base. Alternatives to pure DMSO as solvent include mixtures of DMSO with non-protic or halogenated solvents such as tetrahydrofuran, ethyl acetate, toluene, xylene, dichloromethane, ethylene dichloride and the like. Dipolar aprotic co-solvents include acetonitrile, dimethylformamide, dimethylacetamide, acetamide, tetramethyl urea and its cyclic analog, N-methylpyrrolidone, sulfolane and the like. Rather than N,N-dibenzylphenylalaninol as the aldehyde precursor, the phenylalaninol derivatives discussed above can be used to provide the corresponding N-monosubstituted [either p$^1$ or p$^2$=H] or N,N-disubstituted aldehyde.

In addition, hydride reduction of an amide or ester derivative of the corresponding alkyl, benzyl or cycloalkenyl nitrogen protected phenylalanine, substituted phenylalanine or cycloalkyl analog of phenyalanine derivative can be carried out to provide a compound of Formula III. Hydride transfer is an additional method of aldehyde synthesis under conditions where aldehyde condensations are avoided, cf, Oppenauer Oxidation.

The aldehydes of this process can also be prepared by methods of reducing protected phenylalanine and phenylalanine analogs or their amide or ester derivatives by, e.g., sodium amalgam with HCl in ethanol or lithium or sodium or potassium or calcium in ammonia. The reaction temperature may be from about −20° C. to about 45° C., and preferably from abut 5° C. to about 25° C. Two additional methods of obtaining the nitrogen protected aldehyde include oxidation of the corresponding alcohol with bleach in the presence of a catalytic amount of 2,2,6,6-tetramethyl-1-pyridyloxy free radical. In a second method, oxidation of the alcohol to the aldehyde is accomplished by a catalytic amount of tetrapropylammonium perruthenate in the presence of N-methylmorpholine-N-oxide.

Alternatively, an acid chloride derivative of a protected phenylalanine or phenylalanine derivative as disclosed above can be reduced with hydrogen and a catalyst such as Pd on barium carbonate or barium sulphate, with or without an additional catalyst moderating agent such as sulfur or a thiol (Rosenmund Reduction).

An important aspect of the present invention is a reaction involving the addition of chloromethyllithium or bromomethyllithium to the α-amino aldehyde. Although addition of chloromethyllithium or bromomethyllithium to aldehydes is known, the addition of such species to racemic or chiral amino aldehydes to form aminoepoxides of the formula

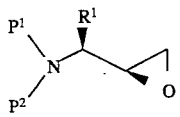

is novel. The addition of chloromethyllithium or bromomethyllithium to a chiral amino aldehyde is highly diastereoselective. Preferably, the chloromethyllithium or bromomethyllithium is generated in-situ from the reaction of the dihalomethane and n-butyllithium. Acceptable methyleneating halomethanes include chloroiodomethane, bromochloromethane, dibromomethane, diiodomethane, bromofluoromethane and the like. The sulfonate ester of the addition product of, for example, hydrogen bromide to formaldehyde is also a methyleneating agent. Tetrahydrofuran is the preferred solvent, however alternative solvents such as toluene, dimethoxyethane, ethylene dichloride, methylene chloride can be used as pure solvents or as a mixture. bipolar aprotic solvents such as acetonitrile, DMF, N-methylpyrrolidone are useful as solvents or as part of a solvent mixture. The reaction can be carried out under an inert atmosphere such as nitrogen or argon. For n-butyl lithium can be substituted other organometalic reagents reagents such as methyllithium, tert-butyl lithium, sec-butyl lithium, phenyllithium, phenyl sodium and the like. The reaction can be carried out at temperatures of between about −80° C. to 0° C. but preferably between about −80° C. to −20° C. The most preferred reaction temperatures are between −40° C. to −15° C. Reagents can be added singly but multiple additions are preferred in certain conditions. The preferred pressure of the reaction is atmospheric however a positive pressure is valuable under certain conditions such as a high humidity environment.

Alternative methods of conversion to the epoxides of this invention include substitution of other charged methylenation precurser species followed by their treatment with base to form the analogous anion. Examples of these species include trimethylsulfoxonium tosylate or triflate, tetramethylammonium halide, methyldiphenylsulfoxonium halide wherein halide is chloride, bromide or iodide.

The conversion of the aldehydes of this invention into their epoxide derivative can also be carried out in multiple steps. For example, the addition of the anion of thioanisole prepared from, for example, a butyl or aryl lithium reagent, to the protected aminoaldehyde, oxidation of the resulting protected aminosulfide alcohol with well known oxidizing agents such as hydrogen peroxide, tert-butyl hypochlorite, bleach or sodium periodate to give a sulfoxide. Alkylation of the sulfoxide with, for example, methyl iodide or bromide, methyl rosylate, methyl mesylate, methyl triflate, ethyl bromide, isopropyl bromide, benzyl chloride or the like, in the presence of an organic or inorganic base Alternatively, the protected aminosulfide alcohol can be alkylated with, for example, the alkylating agents above, to provide sulfonium salts that are subsequently converted into the subject epoxides with tert-amine or mineral bases.

The desired epoxides form, using most preferred conditions, diastereoselectively in ratio amounts of at least about an 85:15 ratio (S:R). The product can be purified by chromatography to give the diastereomerically and enantiomerically pure product but it is more conveniently used directly without purification to prepare HIV protease inhibitors.

This process is applicable to mixtures of optical isomers as well as resolved compounds. If a particular optical isomer is desired, it can be selected by the choice of starting material, e.g., L-phenylalanine, D-phenylalanine, L-phenylalaninol, D-phenylalaninol, D-hexahydrophenylalaninol and the like, or resolution can occur at intermediate or final steps. Chiral auxiliaries such as one or two equivilants of camphor sulfonic acid, citric acid, camphoric acid, 2-methoxyphenylacetic acid and the like can be used to form salts, esters or amides of the compounds of this invention. These compounds or derivatives can be crystallized or separated chromatographically using either a chiral or achiral column as is well known to those skilled in the art.

A further advantage of the present process is that materials can be carried through the above steps without purification of the intermediate products. However, if purification is desired, the intermediates disclosed can be prepared and stored in a pure state.

The practical and efficient synthesis described here has been successfully scaled up to prepare large quantity of intermediates for the preparation of HIV protease inhibitors. It offers several advantages for multikilogram preparations: (1) it does not require the use of hazardous reagents such as diazomethane, (2) it requires no purification by chromatography, (3) it is short and efficient, (4) it utilizes inexpensive and readily available commercial reagents, (5) it produces enantiomerically pure alpha amino epoxides. In particular, the process of the invention produces enantiomerically-pure epoxide as required for the preparation of enantiomerically-pure intermediate for further synthesis of HIV protease inhibitors.

The amino epoxides were prepared utilizing the following procedure as disclosed in Scheme II below.

Scheme II

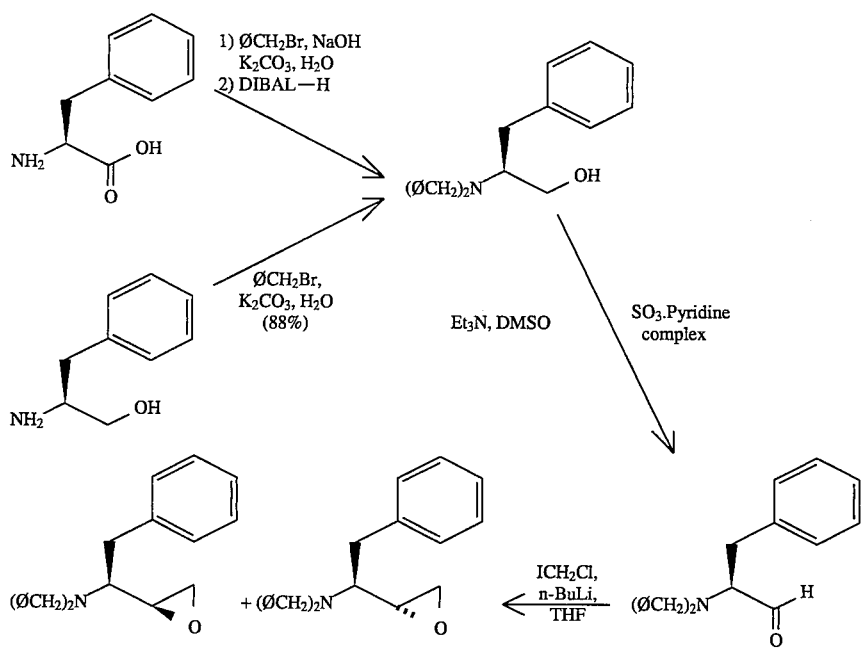

In Scheme II, there is shown a synthesis for the epoxide, chiral N, N,α-S-tris(phenylmethyl)-2S-oxiranemethanamine. The synthesis starts from L-phenylalanine. The aldehyde is prepared in three steps from L-phenylalanine or phenylalinol. L-Phenylalanine is converted to the N,N-dibenzylamino acid benzyl ester using benzyl bromide under aqueous conditions. The reduction of benzyl ester is carried out using diisobutylaluminum hydride (DIBAL-H) in toluene. Instead of purification by chromatography, the product is purified by an acid (hydrochloric acid) quench of the reaction, the hydrochloride salt is filtered off as a white solid and then liberated by an acid/base extraction. After one recrystallization, chemically and optically pure alcohol is obtained. Alternately, and preferably, the alcohol can be obtained in one step in 88% yield by the benzylation of L-phenylalaninol using benzylbromide under aqueous conditions. The oxidation of alcohol to aldehyde is also modified to allow for more convenient operation during scaleup. Instead of the standard Swern procedures using oxalyl chloride and DMSO in methylene chloride at low temperatures (very exothermic reaction), sulfur trioxide-pyridine/DMSO was employed (Parikh, J., Doering, W., *J. Am. Chem. Soc.*, 89, p. 5505, 1967) which can be conveniently performed at room temperature to give excellent yields of the desired aldehyde with high chemical and enantiomer purity which does not require purification.

An important reaction involves the addition of chloromethyllithium or bromomethyllithium to the aldehyde. Although addition of chloromethyllithium or bromomethyllithium to aldehydes has been reported previously, the addition of such species to chiral α-amino aldehydes to form chiral-aminoepoxides is believed to be novel. Now, chloromethyllithium or bromomethyllithium is generated in-situ from chloroiodomethane(or bromochloromethane) or dibromomethane and n-butyllithium at a temperature in a range from about −78° C. to about −10° C. in THF in the presence of aldehyde. The desired chlorohydrin or bromohydrin is formed as evidenced by TLC analyses. After warming to room temperature, the desired epoxide is formed diastereoselectively in a 85:15 ratio (S:R). The product can be purified by chromatography to give the diastereomerically pure product as a colorless oil but it is more conveniently used directly without purification.

EXAMPLE 1

β2- [Bis(phenylmethyl)amino]benzenepropanol

METHOD 1

Step 1: Benzylation of L-Phenylalanine

A solution of L-phenylalanine (50.0 g, 0.302 mol), sodium hydroxide (24.2 g, 0.605 mol) and potassium carbonate (83.6 g, 0.605 mol) in water (500 mL) was heated to 97° C. Benzyl bromide (108.5 mL, 0.605 mol) was then slowly added (addition time—25 min). The mixture was stirred at 97° C. for 30 minutes under a nitrogen atmosphere. The solution was cooled to room temperature and extracted with toluene (2×250 mL). The combined organic layers were washed with water and brine, dried over magnesium sulfate, filtered and concentrated to an oil. The identity of the product was confirmed as follows. Analytical TLC (10% ethyl acetate/hexane, silica gel) showed major component at Rf value=0.32 to be the desired tribenzylated compound, N,N-bis(phenylmethyl)-L-phenylalanine phenylmethyl ester. This compound can be purified by column chromatography (silica gel, 15% ethyl acetate/hexanes). Usually the product is pure enough to be used directly in the next step without further purification. $^1$H NMR spectrum was in agreement with published literature. $^1$H NMR (CDCL$_3$) $\partial$, 3.00 and 3.14 (ABX-system, 2H, $J_{AB}$=14.1 Hz, $J_{AX}$=7.3 Hz and $J_{BX}$=5.9 Hz), 3.54 and 3.92 (AB-System, 4 H, $J_{AB}$=13.9 Hz), 3.71 (t, 1H, J=7.6 Hz), 5.11 and 5.23 (AB-System, 2H, $J_{AB}$=12.3 Hz), and 7.18 (m, 20 H). EIMS: m/z 434 (M-1).

Step 2:
βS-2-[Bis(phenylmethyl)amino]benzenepropanol from the DIBAL Reduction of N,N-bis (phenylmethyl)-L-Phenylalanine phenylmethyl ester The benzylated phenylalanine phenylmethyl ester (0.302 mol) from the previous reaction was dissolved in toluene (750 mL) and cooled to −55° C. A 1.5M solution of DIBAL in toluene (443.9 mL, 0.666 mol) was added at a rate to maintain the temperature between −55° to −50° C. (addition time—1 hr). The mixture was stirred for 20 minutes under a nitrogen atmosphere and then quenched at −55° C. by the slow addition of methanol (37 ml). The cold solution was then poured into cold (5° C.) 1.5N HCl solution (1.8 L). The precipitated solid (approx. 138 g) was filtered off and washed with toluene. The solid material was suspended in a mixture of toluene (400 mL) and water (100 ml). The mixture was cooled to 5° C. and treated with 2.5N NaOH (186 mL) and then stirred at room temperature until solid dissolved. The toluene layer was separated from the aqueous phase and washed with water and brine, dried over magnesium sulfate, filtered and concentrated to a volume of 75 mL (89 g). Ethyl acetate (25 mL) and hexane (25 mL) were added to the residue upon which the desired alcohol product began to crystallize. After 30 min, an additional 50 mL hexane were added to promote further crystallization. The solid was filtered off and washed with 50 mL hexane to give 34.9 g of first crop product. A second crop of product (5.6 g) was isolated by refiltering the mother liquor. The two crops were combined and recrystallized from ethyl acetate (20 mL) and hexane (30 mL) to give 40 g of βS-2-[Bis(phenyl-methyl)amino] benzenepropanol, 40% yield from L-phenylalanine. An additional 7 g (7%) of product can be obtained from recrystallization of the concentrated mother liquor. TLC of product Rf=0.23 (10% ethyl acetate/hexane, silica gel); $^1$H NMR (CDCl$_3$) ∂2.44 (m, 1H,), 3.09 (m, 2H), 3.33 (m, 1H), 3.48 and 3.92 (AB-System, 4H, $J_{AB}$=13.3 Hz), 3.52 (m, 1H) and 7.23 (m, 15H); $[\alpha]_D$25+42.4 (c 1.45, CH$_2$Cl$_2$); DSC 77.67° C.; Anal. Calcd. for C$_{23}$H$_{25}$ON: C, 83.34; H, 7.60; N, 4.23. Found: C, 83.43; H, 7.59; N, 4.22. HPLC on chiral stationary phase: Cyclobond I SP column (250×4.6 mm I.D.), mobile phase: methanol/triethyl ammonium acetate buffer pH 4.2 (58:42, v/v), flow-rate of 0.5 ml/min, detection with detector at 230 nm and a temperature of 0° C. Retention time: 11.25 min., retention time of the desired product enantiomer: 12.5 min.

METHOD 2

Preparation of βS-2-[Bis(phenylmethyl)amino]benzenepropanol from the N,N-Dibenzylation of L-Phenylaninol L-phenylaninol (176.6 g, 1.168 mol) was added to a stirred solution of potassium carbonate (484.6 g, 3.506 mol) in 710 mL of water. The mixture was heated to 65° C. under a nitrogen atmosphere. A solution of benzyl bromide (400 g, 2.339 mol) in 3A ethanol (305 mL) was added at a rate that maintained the temperature between 60°–68° C. The biphasic solution was stirred at 65° C. for 55 min and then allowed to cool to 10° C. with vigorous stirring. The oily product solidified into small granules. The product was diluted with 2.0 L of tap water and stirred for 5 minutes to dissolve the inorganic by products. The product was isolated by filtration under reduced pressure and washed with water until the pH is 7. The crude product obtained was air dried overnite to give a semi-dry solid (407 g) which was recrystallized from 1.1 L of ethyl acetate/heptane (1:10 by volume). The product was isolated by filtration (at −8° C.), washed with 1.6 L of cold (−10° C.) ethyl acetate/heptane (1:10 by volume) and air-dried to give 339 g (88% yield) of βS-2-[Bis(phenylmethyl)amino]benzenepropanol, mp 71.5°–73.0° C. More product can be obtained from the mother liquor if necessary. The other analytical characterization was identical to compound prepared as described in Method 1.

EXAMPLE 2

METHOD 1

αS-[Bis(phenylmethyl)amino]benzenepropanaldehyde

βS-2-[Bis(phenylmethyl)amino]benzene-propanol (200 g, 0.604 mol) was dissolved in triethylamine (300 mL, 2.15 mol). The mixture was cooled to 12° C. and a solution of sulfur trioxide/pyridine complex (380 g, 2.39 mol) in DMSO (1.6 L) was added at a rate to maintain the temperature between 8°–17° C. (addition time −1.0 h). The solution was stirred at ambient temperature under a nitrogen atmosphere for 1.5 hour at which time the reaction was complete by TLC analysis (33% ethyl acetate/hexane, silica gel). The reaction mixture was cooled with ice water and quenched with 1.6 L of cold water (10°–15° C.) over 45 minutes. The resultant solution was extracted with ethyl acetate (2.0 L), washed with 5% citric acid (2.0 L), and brine (2.2 L), dried over MgSO$_4$ (280 g) and filtered. The solvent was removed on a rotary evaporator at 35°–40° C. and then dried under vaccuum to give 198.8 g of αS-[Bis-(phenylmethyl)amino] benzenepropanaldehyde as a pale yellow oil (99.9%). The crude product obtained was pure enough to be used directly in the next step without purification. The analytical data of the compound were consistent with the published literature. $[\alpha]_D$25=−92.9° (c 1.87, CH$_2$Cl$_2$); $^1$H NMR (400 MHz, CDCl$_3$) ∂, 2.94 and 3.15 (ABX-System, 2H, $J_{AB}$=13.9 Hz, $J_{AX}$=7.3 Hz and $J_{BX}$=6.2 Hz), 3.56 (t, 1H, 7.1 Hz), 3.69 and 3.82 (AB-System, 4H, $J_{AB}$=13.7 Hz), 7.25 (m, 15 H) and 9.72 (s, 1H); HRMS calcd for (M+1) C$_{23}$H$_{24}$NO 330.450, found: 330.1836. Anal. Calcd. for C$_{23}$H$_{23}$ON: C, 83.86; H, 7.04; N, 4.25. Found: C, 83.64; H, 7.42; N, 4.19. HPLC on chiral stationary phase:(S,S) Pirkle-Whelk-O 1 column (250×4.6 mm I.D.), mobile phase: hexane/isopropanol (99.5:0.5, v/v), flow-rate: 1.5 ml/min, detection with UV detector at 210nm. Retention time of the desired S-isomer: 8.75 min., retention time of the R-enanatiomer 10.62 min.

METHOD 2

A solution of oxalyl chloride (8.4 ml, 0.096 mol) in dichloromethane (240 ml) was cooled to −74° C. A solution of DMSO (12.0 ml, 0.155 mol) in dichloromethane (50 ml) was then slowly added at a rate to maintain the temperature at −74° C. (addition time −1.25 hr). The mixture was stirred for 5 min. followed by addition of a solution of the alcohol (0.074 mol) in 100 ml of dichloromethane (addition time −20 min., temp. −75° C. to −68° C.). The solution was stirred at −78° C. for 35 minutes under a nitrogen atmosphere. Triethylamine (41.2 ml, 0.295 mol) was then added over 10 min. (temp. −78° to −68° C.) upon which the ammonium salt precipitated. The cold mixture was stirred for 30 min. and then water (225 ml) was added. The dichloromethane layer was separated from the aqueous phase and washed with water, brine, dried over magnesium sulfate, filtered and concentrated. The residue was diluted with ethyl acetate and hexane and then filtered to further remove the ammonium salt. The filtrate was concentrated to give the desired aldehyde product. The aldehyde was carried on to the next step without purification.

EXAMPLE 3

METHOD 1

N,N, αS-Tris(phenylmethyl)-2S-oxiranemethanamine

A solution of αS-[Bis(phenylmethyl)amino]benzenepropanaldehyde (191.7 g, 0.58 mol) and chloroiodomethane (56.4 mL, 0.77 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyllithium in hexane (1.6M, 365 mL, 0.58 mol) was then added at a rate that maintained the temperature below −25° C. After addition the mixture was stirred at −30° to −35° C. for 10 minutes. More additions of reagents were carried out in the following manner: (1) additional chloroiodomethane (17 mL) was added, followed by n-butyllithium (110 mL) at <−25° C. After addition the mixture was stirred at −30° to −35° C. for 10 minutes. This was repeated once. (2) Additional chloroiodomethane (8.5 mL, 0.11 mol) was added, followed by n-butyllithium (55 mL, 0.088 mol) at <−25° C. After addition the mixture was stirred at −30° to −35° C. for 10 minutes. This was repeated 5 times. (3) Additional chloroiodomethane (8.5 mL, 0.11 mol) was added, followed by n-butyllithium (37 mL, 0.059 mol) at <−25° C. After addition the mixture was stirred at −30° to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material. (The crude product weight was >100%. Due to the relative instability of the product on silica gel, the crude product is usually used directly in the next step without purification). The diastereomeric ratio of the crude mixture was determined by proton NMR: (2S)/(2R): 86:14. The minor and major epoxide diastereomers were characterized in this mixture by tlc analysis (silica gel, 10% ethyl acetate/hexane), Rf=0.29 & 0.32, respectively. An analytical sample of each of the diastereomers was obtained by purification on silica-gel chromatography (3% ethyl acetate/hexane) and characterized as follows:

N,N, αS-Tris(phenylmethyl)-2S-oxiranemethanamine
1H NMR (400 MHz, CDCl$_3$) ∂2.49 and 2.51 (AB-System, 1H, $J_{AB}$=2.82), 2.76 and 2.77 (AB-System, 1H, $J_{AB}$=4.03 ), 2.83 (m, 2H), 2.99 & 3.03 (AB-System, 1H, $J_{AB}$=10.1 Hz), 3.15 (m, 1H), 3.73 & 3.84 (AB-System, 4H, $J_{AB}$=14.00), 7.21 (m, 15H); $^{13}$C NMR (400 MHz, CDCl$_3$) ∂139.55, 129.45, 128.42, 128.14, 128.09, 126.84, 125.97, 60.32, 54.23, 52.13, 45.99, 33.76; HRMS calcd for C$_{24}$H$_{26}$NO (M+1) 344.477, found 344.2003.

N,N, αS-Tris(phenylmethyl)-2R-oxiranemethanamine
$^1$H NMR (300 MHz, CDCl$_3$) ∂2.20 (m, 1H), 2.59 (m, 1H), 2.75 (m, 2H), 2.97 (m, 1H), 3.14 (m, 1H), 3.85 (AB-System, 4H), 7.25 (m, 15H).HPLC on chiral stationary phase: Pirkle-Whelk-O 1 column (250×4.6 mm I.D.), mobile phase: hexane/isopropanol (99.5:0.5, v/v), flow-rate: 1.5 ml/min, detection with UV detector at 210 nm.

Retention time of(8): 9.38 min., retention time of enantiomer of (4): 13.75 min.

METHOD 2

A solution of the crude aldehyde 0.074 mol and chloroiodomethane (7.0 ml, 0.096 mol) in tetrahydrofuran (285 ml) was cooled to −78° C., under a nitrogen atmosphere. A 1.6M solution of n-butyllithium in hexane (25 ml, 0.040 mol) was then added at a rate to maintain the temperature at −75° C. (addition time—15 min.). After the first addition, additional chloroiodomethane (1.6 ml, 0.022 mol) was added again, followed by n-butyllithium (23 ml, 0.037 mol), keeping the temperature at −75° C. The mixture was stirred for 15 min. Each of the reagents, chloroiodomethane (0.70 ml, 0.010 mol) and n-butyllithium (5 ml, 0.008 mol) were added 4 more times over 45 min. at −75° C. The cooling bath was then removed and the solution warmed to 22° C. over 1.5 hr. The mixture was poured into 300 ml of saturated aq. ammonium chloride solution. The tetrahydrofuran layer was separated. The aqueous phase was extracted with ethyl acetate (1×300 ml). The combined organic layers were washed with brine, dried over magnesium sulfate, filtered and concentrated to give a brown oil (27.4 g). The product could be used in the next step without purification. The desired diastereomer can be purified by recrystallization at a subsequent step.

The product could also be purified by chromatography.

METHOD 3

A solution of αS-[Bis(phenylmethyl)amino]benzenepropanaldehyde (178.84 g, 0.54 mol) and bromochloromethane (46 mL, 0.71 mol) in tetrahydrofuran (1.8 L) was cooled to −30° to −35° C. (colder temperature such as −70° C. also worked well but warmer temperatures are more readily achieved in large scale operations) in a stainless steel reactor under a nitrogen atmosphere. A solution of n-butyllithium in hexane (1.6M, 340 mL, 0.54 mol) was then added at a rate that maintained the temperature below −25° C. After addition the mixture was stirred at −30° to −35° C. for 10 minutes. More additions of reagents were carried out in the following manner: (1) additional bromochloromethane (14 mL) was added, followed by n-butyllithium (102 mL) at <−25° C. After addition the mixture was stirred at −30° to −35° C. for 10 minutes. This was repeated once. (2) Additional bromochloromethane (7 mL, 0.11 mol) was added, followed by n-butyllithium (51 mL, 0.082 mol) at <−25° C. After addition the mixture was stirred at −30° to −35° C. for 10 minutes. This was repeated 5 times. (3) Additional bromochloromethane (7 mL, 0.11 mol) was added, followed by n-butyllithium (51 mL, 0.082 mol) at <−25° C. After addition the mixture was stirred at −30° to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material.

From the foregoing detailed description, one skilled in the art can easily ascertain the essential characteristics of this invention, and without departing from the spirit and scope thereof, can make various changes and modifications of the invention to adapt it to various usages and conditions.

What is claimed is:

1. A method of preparing an aminoepoxide compound of Formula I:

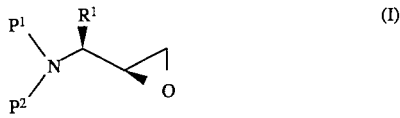

wherein $p^1$ and $p^2$ independently are selected from acyl, aralkyl, alkenyl, silyl, aralkoxycarbonyl, alkoxycarbonyl and cycloalkenylalkyl;

wherein further $p^1$ and $p^2$ may be taken together with the nitrogen atom of Formula I to form a heterocyclic ring system containing said nitrogen atom as a ring member;

and wherein $R^1$ is selected from alkyl, aryl, cycloalkyl, cycloalkylalkyl and aralkyl, which are optionally substituted with a group selected from alkyl, halo, $NO_2$, $OR^9$ and $SR^9$, wherein $R^9$ is selected from hydrogen and alkyl;

and wherein any of the foregoing groups of $p^1$, $p^2$ and $R^1$ may be substituted at one or more substitutable positions with one or more radicals independently selected from halo, alkyl of $C_1$–$C_8$, alkoxy, hydroxy, nitro, alkenyl, amino, alkylamino, acylamino and acyl; or a pharmaceutically-acceptable salt thereof;

said method comprising the steps of forming a protected aminoalcohol, oxidizing said protected aminoalcohol to a chiral protected aminoaldehyde and diastereoselectively forming the aminoepoxide from said aminoaldehyde with an organometallic methylene-adding reagent in an appropriate solvent at a temperature above −80° C.

2. A diastereoselective and enantio selective method of preparing a protected chiral alpha-amino epoxide of Formula I:

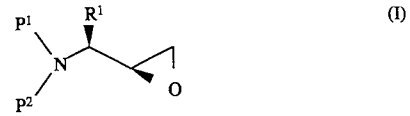

wherein $p^1$ and $p^2$ independently are selected from acyl, aralkyl, alkenyl, silyl, aralkoxycarbonyl, alkoxycarbonyl and cycloalkenylalkyl;

wherein further $p^1$ and $p^2$ may be taken together with the nitrogen atom of Formula I to form a heterocyclic ring system containing said nitrogen atom as a ring member;

and wherein $R^1$ is selected from alkyl, aryl, cycloalkyl, cycloalkylalkyl and aralkyl, which are optionally substituted with a group selected from alkyl, halo, $NO_2$, $OR^9$ and $SR^9$, wherein $R^9$ is selected from hydrogen and alkyl;

and wherein any of the foregoing groups of $p^1$, $p^2$ and $R^1$ may be substituted at one or more substitutable positions with one or more radicals independently selected from halo, alkyl of $C_1$–$C_8$, alkoxy, hydroxy, nitro, alkenyl, amino, alkylamino, acylamino and acyl; or a pharmaceutically-acceptable salt thereof;

said method comprising treating a protected chiral aminoaldehyde substrate with an organometallic methylene-adding reagent in an appropriate solvent at a temperature above −80° C.

3. The method of claim 2 wherein $p^1$ and $p^2$ independently are selected from carbobenzoxy, t-butoxycarbonyl, acetyl, butyryl, benzoyl, isobutyloxycarbonyl, allyl, 1,2-bis(dimethylsilyl)ethane, 1,2-bis(dimethylsilyl)benzene, substituted benzoyl, trifluoroacetyl, trichloroacetyl, phthaloyl, benzyl, ortho-methylbenzyl, trityl, 1,2-bis(methylene)benzene, benzhydryl, phenethyl, phenpropyl, phenyl, naphthalenyl, indenyl, anthracenyl, durenyl, 9-(9-phenyl-fluoroenyl) and phenanthrenyl, wherein further $p^1$ and $p^2$ may be taken together to form with the nitrogen atom of Formula I a radical selected from phthalimide, succinimide and maleimide, and wherein any of the foregoing groups of $p^1$ and $p^2$ may be substituted at one or more substitutable positions with one or more radicals independently selected from halo, alkyl of $C_1$–$C_8$, alkoxy, hydroxy, nitro, alkenyl, amino, alkylamino, acylamino and acyl; or a pharmaceutically-acceptable salt thereof.

4. The method of claim 2 wherein $p^1$ and $p^2$ are independently selected from aralkyl, 1-2-bis(methylene)benzene and aralkyl substituted with one or more radicals independently selected from halo, alkyl of $C_1$–$C_8$, alkoxy, hydroxy, nitro, alkenyl, amino, alkylamino, acylamino and acyl; and wherein $R^1$ is aralkyl; or a pharmaceutically-acceptable salt thereof.

5. The method of claim 2 wherein the organometallic methylene-adding reagent is a halomethyllithium generated in situ.

6. The method of claim 5 wherein at least an equimolar amount of organometallic methylene-adding reagent is added to the aminoaldehyde.

7. The method of claim 5 wherein the halomethyllithium is formed through the addition of an organolithium reagent with a dihalomethane.

8. The method of claim 7 wherein the dihalomethane is selected from bromochloromethane, chloroiodomethane, dibromomethane, diiodomethane and bromofluoromethane.

9. The method of claim 5 wherein the halomethyllithium is added to the amino aldehyde at a temperature in a range of about −80° C. to about 0° C.

10. The method of claim 5 wherein the halomethyllithium is added to the amino aldehyde at a temperature in a range of about −40° C. and −15° C.

11. The diastereoselective method of preparing protected chiral alpha-amino epoxides of claim 2 wherein the amino aldehyde is alpha-S-[bis(phenylmethyl)amino]-benzenepropanaldehyde.

12. A method according to claim 1 characterized in that the protected chiral alpha-amino alcohol of Formula II:

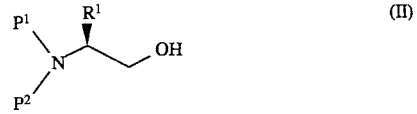

wherein $p^1$, $p^2$ and $R^1$ are defined as indicated in claim 1 is formed by treating an amino acid with an alkylating agent to form a protected-amino acid, and forming a protected amino-alcohol by treating said protected amino acid with a reducing agent in a suitable solvent.

13. The method of claim 12 wherein the reducing agent is diisobutylaluminum hydride.

14. The method of claim 12 wherein said amino acid is L-phenylalanine.

* * * * *

UNITED STATES PATENT AND TRADEMARK OFFICE
CERTIFICATE OF CORRECTION

PATENT NO. : 5,583,238
DATED : December 10, 1996
INVENTOR(S) : Ng et al.

It is certified that error appears in the above-identified patent and that said Letters Patent is hereby corrected as shown below:

Column 1,
Line 2, change "24, 1993" to -- 20, 1993 --.

Signed and Sealed this

Seventeenth Day of August, 2004

JON W. DUDAS
*Acting Director of the United States Patent and Trademark Office*